US005721100A

United States Patent [19]

Polymeropoulos et al.

[11] Patent Number: 5,721,100

[45] Date of Patent: *Feb. 24, 1998

[54] THREE HIGHLY INFORMATIVE MICROSATELLITE REPEAT POLYMORPHIC DNA MARKERS

[75] Inventors: Mihael H. Polymeropoulos, Bethesda; Carl R. Merril, Rockville, both of Md.

[73] Assignee: The United States of America as represented by the Secretary of the Department of Health and Human Services, Washington, D.C.

[*] Notice: The term of this patent shall not extend beyond the expiration date of Pat. No. 5,468,610.

[21] Appl. No.: 480,366

[22] Filed: Jun. 7, 1995

Related U.S. Application Data

[63] Continuation of Ser. No. 74,275, Jun. 9, 1993, Pat. No. 5,468,610, which is a continuation of Ser. No. 707,501, May 29, 1991, abandoned.

[51] Int. Cl.$^6$ .............................. C12Q 1/68; C12P 19/34; C07H 21/04
[52] U.S. Cl. .................... 435/6; 435/91.2; 536/24.31; 536/24.33
[58] Field of Search .................. 435/6, 91.2; 536/24.33, 536/24.31, 24.3

[56] References Cited

U.S. PATENT DOCUMENTS

| | | | |
|---|---|---|---|
| 4,683,202 | 7/1987 | Mullis et al. | 435/91.2 |
| 4,879,214 | 11/1989 | Kornher et al. | 435/6 |
| 5,001,050 | 3/1991 | Blanco et al. | 435/6 |
| 5,468,610 | 11/1995 | Polymeropoulos et al. | 435/6 |

OTHER PUBLICATIONS

Weber et al., Nucleic Acids Res. (1990) 18:(15):4637.
Tautz et al., Nucleic Acids Res (1984)12(10):4127–4138.
Nakamura et al. Science 235 (1987):1616–1622.
Jeffreys et al. Nature 314 (1985):67–73.
Weber et al. (1989) American J. Hum. Genet. 44:388–396.
Polymeropoulos et al. (Feb. 11,1991) Nucleic Acids Res. vol. 19(3), p. 689.

*Primary Examiner*—Lisa B. Arthur
*Attorney, Agent, or Firm*—Spencer & Frank

[57] ABSTRACT

The invention relates to polymorphic markers (two tetranucleotide and one dinucleotide repeat polymorphisms) that are useful for human individualization. Applications are in forensic medicine and for paternity and prenatal screening as well as genetic mapping. These markers are characterized by sets of oligonucleotide primers according to the invention useful in PCR amplification and DNA segment resolution. The invention further relates to an assay for measuring the subtle differences in genetic material regarding an added or omitted set of dinucleotide or tetranucleotide repeat polymorphisms which comprises obtaining an amount of nucleotide segments effective for testing, amplifying the segments by the PCR procedure using at least one primer nucleotide sequence according to the present invention, resolving the amplified segments using gel electrophoresis, and comparing the resolved segments by autoradiography to observe the differences in migration patterns due to structural differences. The assay according to the invention is easy to perform and results can be obtained within 24 hours. It is not uncommon for results to be available within 3–4 hours. Accordingly, the invention also relates to an improved PCR procedure and a PCR assay kit which comprise nucleotides according to the invention.

12 Claims, 2 Drawing Sheets

FIGURE 1

AATCTGGGCG ACAAGAGTGA  20

FIGURE 2

ACATCTCCCC TACCGCTATA  20

FIGURE 3

TCCAGCCTCG GAGACAGAAT  20

FIGURE 4

AGTCCTTTCT CCAGAGCAGG T  21

FIGURE 5

GCCAGTGATG CTAAAGGTTG  20

FIGURE 6

AACATACGTG GCTCTATGCA  20

FIGURE 7

| | | | | | |
|---|---|---|---|---|---|
| AATCTGGGCG | ACAAGAGTGA | AACTCCGTCA | AAAGAAAGAA | AGAAAGAGAC | 50 |
| AAAGAGAGTT | AGAAAGAAAG | AAAGAGAGAG | AGAGAGAAAG | GAAGGAAGGA | 100 |
| AGAAAAAGAA | AGAAAAAGAA | AGAAAGAGAA | AGAAAGAAAG | AGAAAGAAAG | 150 |
| AAAGAAAGAA | AGAAAGAAAG | AAAGAAAGAA | AGAAAGAAAA | AGAAAGAAAG | 200 |
| AAAGAAAGAA | AGAAAGAAAG | AAAGAAAGAA | AGAAAGAAAG | AAAGAAAGGA | 250 |
| AGGAAAGAAA | GAGCAAGTTA | CTATAGCGGT | AGGGGAGATG | T | 291 |

FIGURE 8

| | | | | | |
|---|---|---|---|---|---|
| GCCAGTGATG | CTAAAGGTTG | TATTGCATAT | ATACATATAT | ATATATATAT | 50 |
| ATATATATAT | ATATATATAT | ATATATATAT | ATATATATAT | TTTAATTTGA | 100 |
| TAGTATTGTG | CATAGAGCCA | CGTATGTT | | | 128 |

FIGURE 9

| | | | | | |
|---|---|---|---|---|---|
| TCCAGCCTCG | AGACAGAAT | GAGACTCCAT | CAAAAACAAG | AAAGAAAGAA | 50 |
| AGACAAAGAG | AGAAAGAAAG | AAAGAAAGAA | AGAAAGAAAG | AGAGAGAGAG | 100 |
| AGAGAGAGAG | AGAAAGAAAG | AAAGAAAGAA | AGAAAGAAAG | AAAGAAAGAA | 150 |
| AGAAAGAAAG | AAAGAAAGAA | GGAAAGAAAG | AAAGGAAACT | AAAATAACTA | 200 |
| AATAACTGAG | TAGCACCACA | CCACCTGCTC | TGGAGAAAGG | ACT | 243 | ic DNA markers having repeat sequences to provide a
THREE HIGHLY INFORMATIVE MICROSATELLITE REPEAT POLYMORPHIC DNA MARKERS This application is a continuation of U.S. patent application Ser. No. 08/074,275, filed Jun. 9, 1993, now issued as U.S. Pat. No. 5,468,610, which is a continuation of U.S. patent application Ser. No. 07/707,501, filed May 29, 1991, now abandoned.

TECHNICAL FIELD

This application relates to genetic testing with polymorphic DNA markers having repeat sequences to provide a rapid and convenient high resolution process for distinguishing target nucleic acid segments on the basis of nucleotide differences according to human individualization wherein the nucleic acid segments differ in size.

BACKGROUND ART

The science of genetics has taken a keen interest in the identification of human individualization and genetic relationships between individuals. Each individual has hereditary material (DNA, "nucleotides") which is unique to that individual and hereditary material which is related to that of others. Procedures have been developed which are based on identification and characterization of changes in DNAs, which are changes in DNA (DNA polymorphisms) due to nucleotide substitution, insertion, or deletion within the chains of DNAs.

In the field of forensic medicine, for example, there is a keen interest in such polymorphisms for identification purposes. Forensic geneticist have developed many techniques to compare homologous segments of DNA to determine if the segments are identical or if they differ in one or more nucleotides. Practical applications of these techniques relate to fields other than forensic medicine, for example, genetic disease diagnosis and human genome mapping.

At the present time in this art, the most accurate and informative way to compare DNA segments requires a method which provides the complete nucleotide sequence for each DNA segment. Particular techniques have been developed for determining actual sequences in order to study mutation in human genes. See, for example, Proc. Natl. Acad. Sci. U.S.A. 85, 544–548 (1988) and Nature 330, 384–386 (1987). However, because of the extensive amounts of time and high costs to determine, interpret, and compare sequence information, presently it is not practical to use extensive sequencing for comparing more than just a few DNA segments.

In genetic mapping, the most frequently used screening for DNA polymorphisms arising from mutations consist of digesting the DNA strand with restriction endonucleases and analyzing the resulting fragments by means of Southern blots. See Am. J. Hum. Genet. 32, 314–331 (1980) or Sci. Am. 258, 40–48 (1988). Since mutations often occur randomly they may affect the recognition sequence of the endonuclease and preclude the enzymatic cleavage at that site. Restriction fragment length polymorphism mappings (RFLPS) are based on changes at the restriction site. They are accurate but not very informative (PIC [0.3). The major problem with RFLPs is the inability of a test to detect changes that do not affect cleavage with a restriction endonuclease. As in many of the test methods in the DNA art, the methods used to detect RFLPs are very labor intensive and expensive, especially the techniques which includes Southern blot analysis.

Another technique for detecting specific mutations in particular DNA segment involves hybridizing DNA segments which are being analyzed (target DNA) with a complimentary, labeled oligonucleotide probe. See Nucl. Acids Res. 9, 879–894 (1981). Since DNA duplexes containing even a single base pair mismatch exhibit high thermal instability, the differential melting temperature can be used to distinguish target DNAs that are perfectly complimentary to the probe from target DNAs that only differ by a single nucleotide. This method has been adapted to detect the presence or absence of a specific restriction site. U.S. Pat. No. 4,683,194. The method involves using an end-labeled oligonucleotide probe spanning a restriction site which is hybridized to a target DNA. The hybridized duplex of DNA is then incubated with the restriction enzyme appropriate for that site. Reformed restriction sites will be cleaved by digestion in the pair of duplexes between the probe and target by using the restriction endonuclease. The specific restriction site is present in the target DNA if shortened probe molecules are detected.

Another process for studying differences in DNA structure is the primer extension process which consists of hybridizing a labeled oligonucleotide primer to a template RNA or DNA and then using a DNA polymerase and deoxynucleoside triphosphates to extend the primer to the 5' end of the template. Resolution of the labeled primer extension product is then done by fractionating on the basis of size, e.g., by electrophoresis via a denaturing polyacrylamide gel. This process is often used to compare homologous DNA segments and to detect differences due to nucleotide insertion or deletion. Differences due to nucleotide substitution are not detected since size is the sole criterion used to characterize the primer extension product.

Another process exploits the fact that the incorporation of some nucleotide analogs into DNA causes an incremental shift of mobility when the DNA is subjected to a size fractionation process, such as electrophoresis. Nucleotide analogs can be used to identify changes since they can cause an electrophoretic mobility shift. See, U.S. Pat. No. 4,879,214.

Unfortunately, the above techniques used for identification of polymorphisms are either not very informative or take a long period of time to perform. For example, techniques which identify changes in individual nucleotides on a particular DNA strand often take at least three to four days to perform. Accordingly, such tests are very labor intensive and expensive to perform.

Further, subtle genetic differences among related individuals regarding nucleotides which are substituted in the DNA chains are difficult to detect. VNTR's or Jeffrey's probes (which the FBI is using to test and identify DNA chains) are very informative but labor intensive, in distinction to microsatellites as ours which are equally informative PCR based polymormismic.

The use of certain nucleotide repeat polymorphisms for identifying or comparing DNA segments have been described by Weber & May 89 Am Hum Genet 44:388, Litt & Luthy '89 Am) Hum Genet 44:397). However the particular polymorphism genetic segments and primers used to identify the polymorphisms (for identification and comparison purposes) of the present invention have not been previously known or suspected.

Accordingly, there a need in this art for a rapid, simple, inexpensive and accurate technique having a very high resolution value to determine relationships between individuals and differences in degree of relationships. Also, there is a need in the art for a very accurate genetic relationship test procedure which uses very small amounts of an original DNA sample, yet produces very accurate results. This is particularly true in the forensic medicine area and criminology, since often times very small samples of DNA are available for testing.

DISCLOSURE OF THE INVENTION

An object of the present invention is to provide a fast and accurate test for measuring the subtle differences in individuals by way of genetic testing.

Another object of the invention relates to polymorphic markers (two tetranucleotide and one dinucleotide repeat polymorphisms) that can be used for human individualization.

A further object of the invention is to provide a fast and accurate technique for measuring the subtle differences in individuals by way of genetic testing that can be applied in multiple areas, e.g., forensic screening, paternity and prenatal screening and genetic mapping.

A still further object is to provide an improved method for conducting a PCR procedure using an effective amount of a nucleotide according to the present invention and to provide an PCR assay kit comprising an effective amount of a nucleotide according to the present invention and ancillary PCR reagents.

BRIEF DESCRIPTION OF DRAWINGS

FIG. 1 relates to a nucleotide sequence according to SEQ ID NO:1.

FIG. 2 relates to a nucleotide sequence according to SEQ ID NO:2.

FIG. 3 relates to a nucleotide sequence according to SEQ ID NO:3.

FIG. 4 relates to a nucleotide sequence according to SEQ ID NO:4.

FIG. 5 relates to a nucleotide sequence according to SEQ ID NO:5.

FIG. 6 relates to a nucleotide sequence according to SEQ ID NO:6.

FIG. 7 relates to a nucleotide sequence according to SEQ ID NO:7.

FIG. 8 relates to a nucleotide sequence according to SEQ ID NO:8.

FIG. 9 relates to a nucleotide sequence according to SEQ ID NO:9.

BEST MODE FOR CARRYING OUT THE INVENTION

The present invention provides a fast and accurate test for measuring subtle genetic differences in individuals by way of genetic testing. The invention further relates to polymorphic markers (two tetranucleotide and one dinucleotide repeat polymorphisms) that can be used for human individualization. Applications for the technique and markers according to the invention are for example, in forensic screening, in paternity and prenatal screening as well as in genetic mapping.

The invention relates to polymorphic markers (two tetranucleotide and one dinucleotide repeat polymorphisms) that are useful for human individualization of forensic screen, and for paternity and prenatal screening as well as genetic mapping. The markers according to the present invention have high polymorphism information content (PIC) values.

These markers are characterized by sets of oligonucleotide primers as follows:

1. Set 1, PIC 0.92
    a. A nucleotide sequence according to SEQ ID NO:1
    b. A nucleotide sequence according to SEQ ID NO:2
2. Set 2, PIC 0.91
    a. A nucleotide sequence according to SEQ ID NO:3
    b. A nucleotide sequence according to SEQ ID NO:4
3. Set 3, PIC 0.92
    a. A nucleotide sequence according to SEQ ID NO:5
    b. A nucleotide sequence according to SEQ ID NO:6.

These polymorphic markers (two tetranucleotide and one dinucleotide repeat polymorphisms which are also accompanied by beginning and ending nucleotide sequences) that can be used for human individualization are further characterized by the following marker sequences.

1. A nucleotide sequence having a repeat polymorphism according to SEQ ID NO:7.
2. A nucleotide sequence having a repeat polymorphism according to SEQ ID NO:8.
3. A nucleotide sequence having a repeat polymorphism according to SEQ ID NO:9.

Since a polymorphic marker and an index locus occur as a "pair", attaching a primer oligonucleotide according to the present invention to the polymorphic marker allows PCR amplification of the segment pair. The amplified DNA segment can then be resolved by electrophoresis and autoradiography. A resulting autoradiography can then be analyzed for its similarity to another DNA segment autoradiography. Following the PCR amplification procedure, electrophoretic motility enhancing DNA analogs may optionally be used to increase the accuracy of the electrophoresis step.

Also, the invention relates to a method for conducting a PCR procedure comprising using an effective amount of at least one nucleotide according to according to the invention as set forth above, wherein the nucleotide is part of a primer pair of nucleotides selected from the group of nucleotide pairs consisting of a) a nucleotide sequence having the sequence as set forth in SEQ ID NO:1 and a nucleotide sequence as set forth in SEQ ID NO:2;

b) a nucleotide sequence having the sequence as set forth in SEQ ID NO:3 and a nucleotide sequence as set forth in SEQ ID NO:4; and c) a nucleotide sequence having the sequence as set forth in SEQ ID NO:5 and a nucleotide sequence as set forth in SEQ ID NO:6.

Therefore, the invention further relates to an assay for measuring the subtle differences in genetic material regarding an added or omitted set of dinucleotide or tetranucleotide repeat polymorphisms selected from the group consisting of a sequence according to SEQ ID NO:7, a sequence according to SEQ ID NO:8 and a sequence according to SEQ ID NO:9, which comprises a. obtaining nucleotide segments comprising said repeat polymorphisms in an amount effective for testing, b. amplifying said segments by a PCR procedure using a pair of oligonucleotide primers capable of amplifying said polymorphism containing segments, c. resolving the amplified segments using page gels electrophoresis, and d. comparing the resolved segments by autoradiography to observe the differences in migration patterns due to length variation.

Preferably, the invention further relates to an assay for measuring the subtle differences in genetic material regarding an added or omitted set of dinucleotide or tetranucleotide repeat polymorphisms selected from the group consisting of a sequence according to SEQ ID NO:7, a sequence according to SEQ ID NO:8 and a sequence according to SEQ ID NO:9, which comprises a. obtaining nucleotide segments comprising said repeat polymorphisms in an amount effective for testing, b. amplifying said segments by a PCR procedure using the pair of oligonucleotide primers selected from the group consisting of a sequence according to SEQ ID NO:1, a sequence according to SEQ ID NO:2, a sequence according to SEQ ID NO:3, a sequence according to SEQ ID NO:4, a sequence according to SEQ ID NO:5, or a sequence according to SEQ ID NO:6, c. resolving the amplified segments using page gels electrophoresis, and d. comparing the resolved segments by autoradiography to observe the differences in migration patterns due to length variation.

Still further, the invention relates to an assay kit for conducting a PCR procedure comprising an effective amount of at least one nucleotide having a sequence according to the invention as set forth above, wherein the nucleotide is part of a primer pair of nucleotides selected from the group of nucleotide pairs consisting of a) a nucleotide sequence having the sequence as set forth in SEQ ID NO:1 and a nucleotide sequence as set forth in SEQ ID NO:2;

b) a nucleotide sequence having the sequence as set forth in SEQ ID NO:3 and a nucleotide sequence as set forth in SEQ ID NO:4; and c) a nucleotide sequence having the sequence as set forth in SEQ ID NO:5 and a nucleotide sequence as set forth in SEQ ID NO:6, in combination with an effective amount of ancillary PCR reagents.

Accordingly, the above described polymorphisms are useful for human sample individualization, because of their high PIC values. Since the described polymorphic systems are based on the polymerase chain reaction (PCR), only minute (40 nanograms) amounts of genomic DNA are required for each test. The target sequences range from 92 to 310 base pairs so that high molecular weight DNA is not necessary, and common problems such as shearing of DNA will have minimal impact on the performance of the assay. The assay is easy to perform and results can be obtained within 24 hours. It is not uncommon for results to be available within 3-4 hours. By comparison, the prior art methods require a number of days before results are available, usually 3-4 days are required.

Further, the assay according to the invention is able to detect very small differences in nucleotide sequences. A single omission or addition of the repeat sequence will change the mobility due to the electrical nature and molecular weight of the target nucleotide sequence. These differences are clearly visible on the autoradiographs after electrophoresis.

Microsatellite repeat polymorphisms have been shown to be useful tools in DNA analysis. The three polymorphisms described here are original and are based on previously sequenced genes. The two tetranucleotide repeat markers described, can be scored easily since allele sizes differ by four base pairs. The most commonly used technique used in forensic screening is based on minisatellite markers, in distinction to the PCR able microsatellites described in the present invention.

The general PCR technique step is conducted generally as described in U.S. Pat. No. 4,683,195 to Mullis et al and U.S. Pat. No. 4,683,202 to Mullis et al, which are hereby incorporated by reference thereto. Further, electrical motility enhancing DNA analogs can optionally be used during the replication and amplification PCR procedure.

The term "primer" as used herein refers to an oligonucleotide whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primer. For example, depending on the complexity of the target sequence, the oligonucleotide primer typically contains 15–25 or more nucleotides, although it may contain fewer nucleotides. Short primer molecules generally require cooler temperatures to form sufficiently stable hybrid complexes with template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer.

It will be understood that the word primer as used hereinafter may refer to more than one primer, particularly in the case where there is some ambiguity in the information regarding the terminal sequence(s) of the fragment to be amplified.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence.

The oligodeoxyribonucleotide primers need not be exactly complementary to the DNA sequence which is being amplified. It is only necessary that they be able to hybridize to the sequence sufficiently well to be extended by the polymerase enzyme or by whatever other inducing agent is employed.

In addition, the primer can contain as part of its sequence a non-complementary sequence provided that a sufficient amount of the primer contains a sequence which is complementary to the strand to be amplified.

The degree of polymorphism in the genetic segments according to the present invention, which polymorphisms yield highly informative identification test results, is surprising and unexpected. The high PIC value (approximately 0.9) is totally unexpected.

Accordingly, the use of a PCR procedure and PCR primers pairs, such as those primer sequences according to SEQ ID NO:1 to SEQ ID NO:6, to detect the polymorphism DNA segment according to the present invention yields excellent results. Such results are sufficiently accurate and informative to accurately identify DNA segments and determine degrees of relationship between DNA segments of individuals.

Moreover, conducting three sets of PCR procedures on the same DNA segment samples while using a different PCR primer pair according to the present invention for each of the three procedures yields extraordinarily accurate and informative test results. Comparison of the three sets of test results data provides extremely accurate DNA segment identification.

The following examples are provided to more specifically describe the invention which is not limited to the following examples.

The described oligonucleotide primers are used to amplify the target sequences using PCR, under the following conditions:

EXAMPLE 1

The samples of DNA are prepared as follows..

60 ng of genomic DNA are used as template for PCR with 80 ng of each oligonucleotide primer, 0.6 units of Taq Polymerase 50 mM KCL, 10 mM Tris (pH 8.3), 1.5 mM $MgCl_2$, 0.01% gelatin, 200 uM of each dGTP, dATP, dTTP, 2.5 uM dCTP and 10 microcuries of alpha P32 dCTP, in a final reaction volume of 15 microliters. The samples are overlayed with 15 microliters of mineral oil to prevent evaporation.

EXAMPLE 2

PCR is performed for each of the samples and primers described in Example 1, above.

PCR is performed in a Techne MW-1 microplate thermocycler under the following conditions denaturation of 94 degrees C. for 1.4 min., annealing at 55 degrees C. for 2 min., and extension at 72 degrees C. for 2 min. The cycle is repeated 30 times with a final extension at 72 degrees C. for 10 min.

EXAMPLE 3

The amplified DNA segments from each of the samples described in Example 2 above are resolved by electrophoresis as follows.

Two microliters of each PCR reaction mixture sample are electrophoresed on a 6% PAGE sequencing gel and visualized by autoradiography. Exposure times for the autoradiography range from 3–16 hours.

---

We claim:

1. An oligonucleotide having a nucleotide sequence selected from the group consisting of SEQ ID NO:1, SEQ ID NO:2, SEQ ID NO:3, SEQ ID NO:4, SEQ ID NO:5, SEQ ID NO:6, and variants of said sequences wherein the variants are from about 15 to 25 nucleotides in length, provided that said variants have sufficient complementarity to a complement sequence of said nucleotide sequence so as to be able to specifically hybridize with said complement sequence sufficiently well to permit primer extension by a polymerase enzyme.

2. A nucleotide sequence according to claim 1, wherein the sequence is a sequence according to SEQ ID NO:1.

3. A nucleotide sequence according to claim 1, wherein the sequence is a sequence according to SEQ ID NO:2.

4. A nucleotide sequence according to claim 1, wherein the sequence is a sequence according to SEQ ID NO:3.

5. A nucleotide sequence according to claim 1, wherein the sequence is a sequence according to SEQ ID NO:4.

6. A nucleotide sequence according to claim 1, wherein the sequence is a sequence according to SEQ ID NO:5.

7. A nucleotide sequence according to claim 1, wherein the sequence is a sequence according to SEQ ID NO:6.

8. A method for conducting a polymerase chain reaction procedure to detect dinucleotide or tetranucleotide repeats in a test sample comprising a nucleic acid and resulting in a polymorphism information content of about 0.9, said method comprising using a pair of oligonucleotide primers in an effective amount for the PCR amplification of a DNA fragment, said oligonucleotide primers comprising at least two oligonucleotides according to claim 1, wherein the oligonucleotides are part of a primer pair selected from the groups consisting of:

a) a sequence as set forth in SEQ ID NO:1 and a sequence as set forth in SEQ ID NO:2;

b) a sequence as set forth in SEQ ID NO:3 and a sequence as set forth in SEQ ID NO:4;

c) a sequence as set forth in SEQ ID NO:5 and a sequence as set forth in SEQ ID NO:6;

and variants of said primer pairs wherein the variants are from about 15 to about 25 nucleotides in length, provided that said variants have sufficient complementarity to a complement sequence of a sequence of the primer pair so as to be able to specifically hybridize with said complement sequence sufficiently well to permit primer extension by a polymerase enzyme.

9. An assay for detecting dinucleotide or tetranucleotide repeats in a sample comprising a nucleic acid, wherein said nucleic acid comprises a sequence selected from the group consisting of SEQ ID NO:7, SEQ ID NO:8, SEQ ID NO:9 and naturally occurring homologues thereof, which assay comprises a) obtaining a nucleic acid sample comprising dinucleotide or tetranucleotide repeats in an amount sufficient for testing by PCR.

b) amplifying specific DNA fragments in said sample by PCR using a pair of oligonucleotide primers capable of amplifying said dinucleotide or tetranucleotide repeats, said oligonucleotide primers having sequences selected from the group consisting of SEQ ID NO:1, SEQ ID NO:2, SEQ ID NO:3, SEQ ID NO:4, SEQ ID NO:5, SEQ ID NO:6 and variants thereof which are from about 15 to about 25 nucleotides in length, provided that said variants have sufficient complementarity to a complement sequence of said nucleotide sequence so as to be able to specifically hybridize with said complement sequence sufficiently well to permit primer extension by a polymerase enzyme, c) resolving the amplified fragments using polyacrylamide gel electrophoresis, and d) detecting the migration patterns of said amplified fragments due to length variation resulting from said dinucleotide or tetranucleotide repeats.

10. An assay according to claim 9, wherein said pair of oligonucleotide primers is selected from the group consisting of a sequence according to SEQ ID NO:1, a sequence according to SEQ ID NO:2, a sequence according to SEQ ID NO:3, a sequence according to SEQ ID NO:4, a sequence according to SEQ ID NO:5, or a sequence according to SEQ ID NO:6.

11. An assay kit including a primer pair of oligonucleotides for conducting PCR comprising an effective amount of at least one oligonucleotide having a sequence according to claim 1, wherein the oligonucleotide is part of a primer pair of oligonucleotides selected from the group of oligonucleotide pairs consisting of:

a) an oligonucleotide comprising the sequence as set forth in SEQ ID NO:1 and an oligonucleotide comprising the sequence set forth in SEQ ID NO:2;

b) an oligonucleotide comprising the sequence as set forth in SEQ ID NO:3 and an oligonucleotide comprising the sequence as set forth in SEQ ID NO:6;

c) an oligonucleotide comprising the sequence as set forth in SEQ ID NO:5 and an oligonucleotide comprising the sequence as set forth in SEQ ID NO:6;

and variants of said oligonucleotides wherein the variants are from about 15 to about 25 nucleotides in length, provided that said variants have sufficient complementarity to a complement sequence of the oligonucleotide sequence so as to be able to specifically hybridize with said complement sequence sufficiently well to permit primer extension by a polymerase enzyme, in combination with an effective amount of ancillary PCR reagents.

12. A method of correlating the source of a test sample comprising a nucleic acid with an individual, said method comprising a) obtaining a nucleic acid sample from an individual, b) performing PCR amplification of the nucleic acid sample obtained in step a) using at least one pair of oligonucleotide primers having sequences selected from the group consisting of the pairs of (i) SEQ ID NO:1 and SEQ ID NO:2, (ii) SEQ ID NO:3 and SEQ ID NO:4, and (iii) SEQ ID NO:5 and SEQ ID NO:6, to provide at least one amplified nucleic acid product from said individual;

c) performing PCR amplification of the test sample nucleic acid using at least one pair of oligonucleotide primers having sequences selected from the group consisting of the pairs of (i) SEQ ID NO:1 and SEQ ID NO:2, (ii) SEQ ID NO:3 and SEQ ID NO:4, and (iii) SEQ ID NO:5 and SEQ ID NO:6, to provide at least one amplified product from said test sample, wherein said at least one oligonucleotide primer pair selected is the same as the at least one oligonucleotide primer pair selected in step b);

d) resolving the amplified products of steps b) and c) by gel electrophoresis, and e) comparing the mobility of the amplified products from said individual with the mobility of the amplified products from said test sample, wherein the mobilities compared in step e) provides a measure of the correlation between the source of said test sample and said individual.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AATCTGGGCG ACAAGAGTGA                                     20

( 2 ) INFORMATION FOR SEQ ID NO:2:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ACATCTCCCC TACCGCTATA                                     20

( 2 ) INFORMATION FOR SEQ ID NO:3:

( i ) SEQUENCE CHARACTERISTICS:
        ( A ) LENGTH: 20

( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TCCAGCCTCG GAGACAGAAT                    20

( 2 ) INFORMATION FOR SEQ ID NO:4:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AGTCCTTTCT CCAGAGCAGG T                    21

( 2 ) INFORMATION FOR SEQ ID NO:5:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GCCAGTGATG CTAAAGGTTG                    20

( 2 ) INFORMATION FOR SEQ ID NO:6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AACATACGTG GCTCTATGCA                    20

( 2 ) INFORMATION FOR SEQ ID NO:7:

( i ) SEQUENCE CHARACTERISTICS:
        ( A ) LENGTH: 291
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

AATCTGGGCG ACAAGAGTGA AACTCCGTCA AAAGAAAGAA AGAAAGAGAC AAAGAGAGTT    60

AGAAAGAAAG AAAGAGAGAG AGAGAGAAAG GAAGGAAGGA AGAAAAAGAA AGAAAAAGAA    120

AGAAAGAGAA AGAAAGAAAG AGAAAGAAAG AAAGAAAGAA AGAAAGAAAG AAAGAAAGAA    180

AGAAAGAAAA AGAAAGAAAG AAAGAAAGAA AGAAAGAAAG AAAGAAAGAA AGAAAGAAAG    240

AAAGAAAGGA AGGAAAGAAA GAGCAAGTTA CTATAGCGGT AGGGGAGATG T              291

( 2 ) INFORMATION FOR SEQ ID NO:8:

-continued (i) SEQUENCE CHARACTERISTICS:
    (A) LENGTH: 128
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:8:

```
GCCAGTGATG CTAAAGGTTG TATTGCATAT ATACATATAT ATATATATAT ATATATATAT    60
ATATATATAT ATATATATAT ATATATATAT TTTAATTTGA TAGTATTGTG CATAGAGCCA   120
CGTATGTT                                                            128
```

(2) INFORMATION FOR SEQ ID NO:9:

(i) SEQUENCE CHARACTERISTICS:
    (A) LENGTH: 243
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:9:

```
TCCAGCCTCG GAGACAGAAT GAGACTCCAT CAAAAACAAG AAAGAAAGAA AGACAAAGAG    60
AGAAAGAAAG AAAGAAAGAA AGAAAGAAAG AGAGAGAGAG AGAGAGAGAG AGAAAGAAAG   120
AAAGAAAGAA AGAAAGAAAG AAAGAAAGAA AGAAAGAAAG AAAGAAAGAA GGAAAGAAAG   180
AAAGGAAACT AAAATAACTA AATAACTGAG TAGCACCACA CCACCTGCTC TGGAGAAAGG   240
ACT                                                                 243
```